United States Patent [19]

Horstmann et al.

[11] 4,329,499
[45] May 11, 1982

[54] ALKYLDIPHENYL ETHER-SULPHONIC ACID HYDRAZIDES, THEIR PREPARATION AND THEIR USE AS BLOWING AGENTS

[75] Inventors: Walter Horstmann; Knut Hammerström, both of Bergisch Gladbach, Fed. Rep. of Germany

[73] Assignee: Bayer Aktiengesellschaft, Leverkusen, Fed. Rep. of Germany

[21] Appl. No.: 208,760

[22] Filed: Nov. 20, 1980

[30] Foreign Application Priority Data

Dec. 6, 1979 [DE] Fed. Rep. of Germany ....... 2949069

[51] Int. Cl.³ .......................................... C07C 143/825
[52] U.S. Cl. ....................................... 564/81; 521/95
[58] Field of Search .......................................... 564/81

[56] References Cited

U.S. PATENT DOCUMENTS

| | | | |
|---|---|---|---|
| 2,513,826 | 7/1950 | Sprung et al. | 564/81 |
| 2,552,065 | 5/1951 | Schoene | 564/81 |
| 2,595,017 | 4/1952 | Sprung et al. | 564/81 |
| 2,626,280 | 1/1953 | Hunter | 564/81 |
| 2,626,933 | 1/1953 | Lober et al. | 564/81 |
| 2,640,853 | 6/1953 | Sundholm | 564/81 |
| 2,673,220 | 3/1954 | Hunter | 564/81 |

*Primary Examiner*—Arthur P. Demers
*Attorney, Agent, or Firm*—Sprung, Horn, Kramer & Woods

[57] ABSTRACT

A di- or tri-sulphonic acid hydrazide of an alkylated diphenyl ether, said hydrazide being of the formula

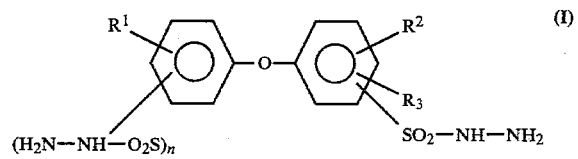

wherein
$R_1$ and $R_2$ are identical or different and represent halogen or a lower alkyl radical and $R_1$ and $R_2$ can denote hydrogen,
$R_3$ denotes a lower alkyl radical and
n represents the number 1 or 2.

A process for the preparation of such hydrazides and the use of such hydrazides as chemical blowing agents in the production of foams from foamable compositions, especially rubbers and thermoplastic resins.

8 Claims, No Drawings

ALKYLDIPHENYL ETHER-SULPHONIC ACID HYDRAZIDES, THEIR PREPARATION AND THEIR USE AS BLOWING AGENTS

The invention relates to new alkyldiphenyl ethersulphonic acid hydrazides, a process for their preparation and their use as blowing agents for the production of porous rubbers and thermoplastic foams.

4,4'-Bis-(hydrazino-sulphonyl-phenyl) ether and its use as a blowing agent for the production of finely porous rubbers and plastics is known from U.S. Pat. No. 2,552,065.

New bis- and tris-sulphonic acid hydrazides of optionally halogenated mono- and di-alkyl-diphenyl ethers, of the formula

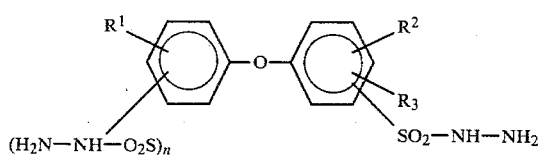

wherein
R$_1$ and R$_2$ are identical or different and represent halogen or a lower alkyl radical and R$_1$ or R$_2$ can denote hydrogen,
R$_3$ denotes a lower alkyl radical and
n represents the number 1 or 2,
have been found.

According to the invention, lower alkyl radicals can be straight-chain or branched hydrocarbon radicals with up to about 4 carbon atoms. Examples which may be mentioned are: methyl, ethyl, propyl, isopropyl, butyl, isobutyl and tertiary butyl. The methyl radical may be mentioned as the preferred lower alkyl radical.

According to the invention, halogen can be fluorine, chlorine, bromine or iodine, preferably chlorine or bromine.

A preferred group of sulphonic acid hydrazides within the scope of the formula (I) comprises compounds of the formula

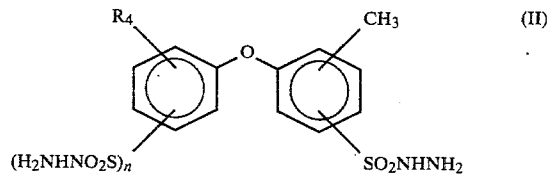

wherein
R$_4$ represents hydrogen, chlorine or methyl and
n represents the number 1 or 2.

Furthermore, a process has been found for the preparation of the new alkyldiphenyl ether-sulphonic acid hydrazides, which is characterized in that alkyldiphenyl ethers are chlorosulphonated with chlorosulphonic acid in the temperature range from 0° to 120° C., if appropriate in the presence of an acid chloride, to give the alkyldiphenyl ether di- or tri-sulphochloride, and this compound is then reacted with hydrazine in a solvent or solvent mixture in the temperature range from 0° to 100° C.

The process according to the invention can be illustrated with the aid of the following equations:

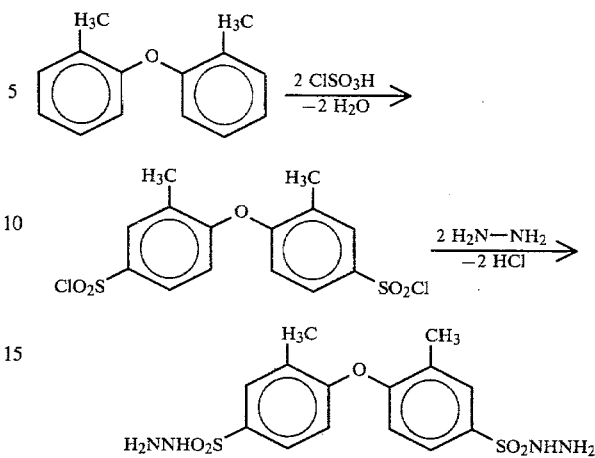

Alkyl-diphenyl ethers for the process according to the invention can be compounds of the formula

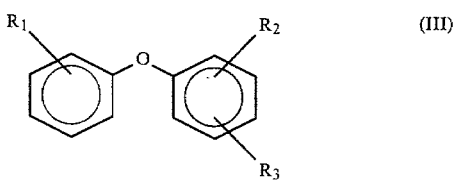

wherein R$_1$, R$_2$ and R$_3$ have the abovementioned meaning.

The monoalkyl-diphenyl ethers used as starting materials can be prepared by reacting halogenobenzenes with alkylphenols or by reacting phenol with alkylhalogenobenzenes (Japanese Pat. No. 104,672). For example, 2-methyl-diphenyl ether is formed from bromobenzene and o-cresol or from phenol and o-chlorotoluene. The dialkyl-diphenyl ethers used are prepared analogously from alkylphenols and alkylhalogenobenzenes, for example 2,2'-dimethyl-diphenyl ether is obtained from o-cresol and o-chlorotoluene. Isomer mixtures of dimethyldiphenyl ethers (ditolyl ethers) are also obtained as by-products of the industrial synthesis of cresol from chlorotoluenes (Industrial and Engineering Chemistry, Volume 38, 254 (1946)). These mixtures can be employed in the process according to the invention either directly or after separation into the pure ditolyl ether isomers by distillation. Alkyl-chlorodiphenyl ethers are obtained, for example, from the reaction of dichlorobenzenes with cresols in the presence of copper catalysts.

The following alkyl-diphenyl ethers are examples of those which can be used: 2-methyl-diphenyl ether, 2-methyl-3'-chlorodiphenyl ether, 3-methyl-3'-chlorodiphenyl ether, 2-ethyl-diphenyl ether, 2,2'-, 2,3'-, 2,4'-, 3,3'-, 3,4'- and 4,4'-ditolyl ether, 2,2'-diethyl-diphenyl ether, 3-methyl-6-chloro-diphenyl ether, 2,5-dimethyl-diphenyl ether, 2,6-dimethyl-diphenyl ether and 3-methyl-6-bromo-diphenyl ether.

The use of chlorosulphonic acid for the process according to the invention is in itself known (Am. Soc. 53, 1112). For complete conversion of the alkyldiphenyl ethers, the reaction is as a rule carried out with excess chlorosulphonic acid. 6 to 12 mols of chlorosulphonic acid are thus in general used per mol of alkyldiphenyl ether.

It has proved advantageous to carry out the reaction with the addition of inorganic acid chlorides, in particular thionyl chloride, in order to avoid a relatively large excess of chlorosulphonic acid.

The chlorosulphonation of the alkyldiphenyl ethers is carried out in the temperature range from 0° to 120° C., preferably from 30° to 80° C., and under normal pressure. It is generally carried out without a solvent or diluent. However, it is also possible to carry out the reaction in solvents such as methylene chloride, chloroform or tetrachloroethane.

In another embodiment of the process according to the invention, the optionally halogenated mono- or di-alkyldiphenyl ethers of the formula (III) are first converted into alkyl-diphenyl ether-di- or -tri-sulphonic acids by sulphonation with sulphuric acid, which may contain sulphur trioxide, and these products, in the form of alkali metal salts, are converted into the corresponding sulphonic acid chlorides with an inorganic acid chloride, such as, for example, phosphorus trichloride or pentachloride or thionyl chloride.

Sulphuric acid with a concentration of over 90% by weight, preferably of 96 to 100% by weight, can be used for the sulphonation, and the sulphonation can be carried out in the temperature range from zero to 150° C., preferably at 40° to 120° C. It is also possible to use oleum containing up to 65% by weight of sulphur trioxide.

The alkyl-diphenyl ether-di- and -tri-sulphonic acid chlorides thus prepared are reacted, according to the invention, with hydrazine in a solvent to give the corresponding di- and tri-sulphonic acid hydrazides. Solvents which may be mentioned are water, lower alcohols, such as methanol, ethanol and isopropanol, methylene chloride, dichloroethane, cyclohexane, toluene, chlorobenzene and mixtures of these solvents.

The hydrazine for the process according to the invention is in general employed in the form of the hydrate.

According to the inventive process the hydrazine is in general employed in an excess. Preferably an excess of 1.2 to 1.7 mols of hydrazine, related to one mol of alkyl-diphenylether sulfonic acid chloride, is employed.

The reaction of the alkyl-diphenyl ethersulphonic acid chlorides with hydrazine is in general carried out in the temperature range from 0° to 100° C., preferably from 10° to 50° C., and under normal pressure; however, it can also be carried out under reduced or increased pressure.

It is advantageous to carry out the reaction of the alkyl-diphenyl ether-sulphonic acid chlorides in the presence of an inorganic base, in order to bond the hydrochloric acid liberated during the reaction and to save hydrazine hydrate.

The process according to the invention can be carried out, for example, as follows:

In a first reaction stage, the alkyl-diphenyl ethers are chlorosulphonated with chlorosulphonic acid and an acid chloride (as a rule thionyl chloride), the reaction mixture is discharged into ice-water and the bis- or tris-sulphonic acid chlorides, which are obtained as crystals, are isolated and washed until free from acid.

In a second reaction stage, hydrazine hydrate is initially introduced, in a suitable solvent or solvent mixture, into the reaction vessel and the bis- or tris-sulphonic acid chloride is added in portions. The reaction mixture is advantageously kept at a pH value of 7 to 11 by dropwise addition of an inorganic base. When the reaction has ended, the mixture is acidified to pH 5 to 6, if necessary, with a mineral acid and the alkyl-diphenyl ether-sulphonic acid hydrazide which has precipitated is filtered off. Because of the instability of these bis- and tris-sulphonic acid hydrazides, they are appropriately dried at temperatures of 30° to 40° C. in vacuo.

The new alkyl-diphenyl ether-sulphonic acid hydrazides according to the invention can be used as blowing agents for the production of sponge rubbers, foam rubbers and cellular rubbers of natural and synthetic rubber and for the production of thermoplastic foams and elastomers. The plastics to be processed, according to the invention, as foams are as a rule prepared by polymerization. The following plastics may be mentioned as examples: polyvinyl chloride, polyethylene, polypropylene, copolymers of vinyl chloride/vinyl acetate, ethylene/vinyl acetate and propylene/vinyl acetate, polystyrene, acrylonitrile/butadiene/styrene polymers (ABS), products based on cellulose esters and mixtures of polyvinyl chloride and ABS polymers or acrylonitrile/butadiene copolymers.

Examples of suitable rubbers for the production of cellular or porous articles using the blowing agents according to the invention are natural rubber or synthetic rubbers. The synthetic polymers are obtained, for example, starting from conjugated diolefins, such as butadiene, chlorobutadiene, dimethylbutadiene or isoprene and its homologs, or they are copolymers of such conjugated diolefines with polymerisable vinyl compounds, such as styrene, α-methylstyrene, acrylonitrile, methacrylonitrile or acrylates. Further synthetic rubbers which are suitable are: ethylene/vinyl acetate copolymers, ethylene/propylene/diene terpolymers, for example with dienes such as 5-ethylidenenorbornene or dicyclopentadiene as the third component, or blends of the polymers mentioned.

The blowing agents according to the invention are preferably used for the production of porous rubber articles.

The blowing agents according to the invention are in general added in amounts of 0.01 to 40% by weight, preferably in amounts of 0.1 to 30% by weight, relative to the resin. It is also possible to use the blowing agents according to the invention in combination with known chemical blowing agents, such as, for example, azodicarboxamide.

To produce the porous resin articles, the blowing agent/resin mixtures are heated to temperatures at which decomposition of the blowing agents with foaming of the resin takes place. For the blowing agents according to the invention, these temperatures are in the range from 100° to 250° C., preferably from 120° to 180° C.

The addition of the blowing agents according to the invention to the mixtures to be foamed can be effected in the customary manner, for example in mixing mills or internal mixers. They can be added at the same time as other constituents of the mixture and auxiliaries are added. Examples of such auxiliaries can be: active or inactive fillers, such as carbon black, silicates, chalk and kaolin, antioxidants, waxes, organic pigments, zinc oxide, fatty acids and fatty acid salts, such as stearic acid and zinc stearate, mineral oils, plasticizers, such as, for example, dioctyl phthalate, butylbenzyl phthalate and tricresyl phosphate, flameproofing agents, such as chloroparaffins, lubricants and vulcanization accelerators, such as, for example, dithiocarbamates.

The following mono- and di-alkyl-diphenyl etherbis- or -tris-sulphonic acid hydrazides are preferably employed as blowing agents in the production of porous resins: 2-methyl-diphenyl ether-4,4'-disulphonic acid hydrazide, 2-methyl-3'-chloro-diphenyl ether-4,4'-disulphonic acid hydrazide, 3-methyl-3'-chloro-diphenyl ether-4,4'-disulphonic acid hydrazide, 3-methyl-6-chlorodiphenyl ether-4,4'-disulphonic acid hydrazide, 3-methyl-6-bromo-diphenyl ether-4,4'-disulphonic acid hydrazide, 2,5-dimethyl-diphenyl ether-4,4'-disulphonic acid hydrazide, 2,6-dimethyl-diphenyl ether-4,4'-disulphonic acid hydrazide, 2,2'-dimethyl-diphenyl ether-4,4'-disulphonic acid hydrazide, 2,3'-dimethyl-diphenyl ether-4,4'-disulphonic acid hydrazide, 3,3'-dimethyl-diphenyl ether-4,4'-disulphonic acid hydrazide, 4,4'-dimethyldiphenyl ether-2,2'-disulphonic acid hydrazide, 2,3'-dimethyl-diphenyl ether-4,4',6'-trisulphonic acid hydrazide and 3,4'-dimethyl-diphenyl ether-4,6,2'-trisulphonic acid hydrazide.

Compared with the blowing agent diphenyl ether-4,4'-disulphonic acid hydrazide known from U.S. Pat. No. 2,552,065, the alkyldiphenyl ethersulphonic acid hydrazides according to the invention have the following surprising advantages: improved capability of preparative and industrial production, for example 2,2'-dimethyldiphenyl ether gives a quantitative yield of a 4,4'-disulphochloride which can be converted, without further purification, into 2,2'-dimethyldiphenyl ether-4,4'-disulphonic acid hydrazide, likewise in high yield and purity. The trisulphonic acid hydrazides according to the invention give a greater yield of nitrogen gas when the same molar amounts are employed. The blowing effect is achieved by the evolution of nitrogen. When compared with diphenyl ether 4,4'-disulphonic acid hydrazide, the advantage of 2,2'-dimethyl-diphenyl ether-4,4'-disulphonic acid hydrazide is, for example, that it produces a PVC foam with a lower specific gravity.

The foams produced with the aid of the blowing agents according to the invention can be employed in the customary manner as plastic foam imitation leather in the upholstery, handbag and luggage and shoe industry, in foamed floor-coverings, in floats of all types, in sheaths for cables, in foamed sheaths for decoration and packaging purposes, in foamed extruded articles, such as tubes and profiles of all types, in foamed injection-moulded articles for the radio, furniture and sound reproduction industry and in sintered rotationally moulded articles.

EXAMPLE 1

198 g (1.0 mol) of 2,2'-ditolyl ether are added dropwise to 933 g (8.0 mols) of chlorosulphonic acid in the course of 1 to 2 hours at a rate such that the internal temperature is kept at 50° C. The mixture is subsequently stirred for 1 hour and 262 g (2.2 mols) of thionyl chloride are then added dropwise at 50°±2° C. in the course of 2 to 3 hours. When the evolution of gas has ended, the mixture is cooled down to room temperature and is discharged slowly onto 4,000 g of water, such that the temperature does not rise above 25° C. The mixture is subsequently stirred for some hours until crystallization is complete and the reaction product is then filtered off and washed until free from mineral acid. After drying at 50° C., 387 g of 2,2'-ditolyl ether-4,4'-disulphochloride are obtained. Melting point: 121° to 123° C. (from xylene/petroleum ether 2/1).

A solution of 150 g (3.0 mols) of hydrazine hydrate in 600 g of water is initially introduced into a 3 l four-necked flask with a stirrer, thermometer, dropping funnel and pH electrode, and 670 g of water-moist 2,2'-ditolyl ether-4,4'-disulphochloride, corresponding to 395 g (1 mol), are introduced at 20° to 25° C. in the course of 1 hour. The pH value is kept at 9 to 9.5 by dropwise addition of 50% strength sodium hydroxide solution. The mixture is subsequently stirred for 1 hour, whilst maintaining a constant pH, and is acidified to pH 5.5 with about 100 g of half-concentrated sulphuric acid. The reaction product is isolated and washed with water until free from chloride. After drying in vacuo at 30° to 35° C., 350 g of 2,2'-ditolyl ether-4,4'-disulphonic acid hydrazide of the formula

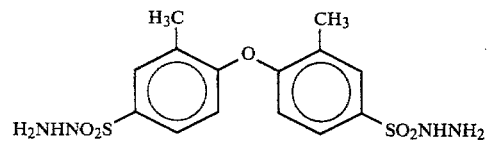

corresponding to 90 to 91% of theory, relative to 2,2'-ditolyl ether, are obtained. Melting point (from ethanol/water): 175° C., with decomposition.

EXAMPLE 2

39.6 g (0.2 mol) of 3,4'-ditolyl ether are reacted with chlorosulphonic acid and thionyl chloride as described in Example 1. The reaction mixture is discharged onto ice-water at 0°–5° C. and the reaction product which has precipitated is isolated and washed until free from acid. After drying in vacuo at 40° C., 66 g of a trisulphochloride mixture are obtained. After dissolving in toluene and reprecipitating with petroleum ether, the product has a melting point of 143°–146° C. Sulphur content: 19.3% (theory: 19.5%). According to the nuclear magnetic resonance spectrum, the reaction product consists of 3,4'-ditolyl ether-2',4,6-trisulphonic acid chloride of the formula

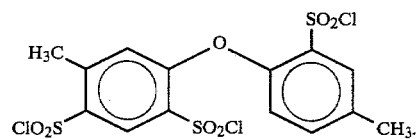

to the extent of about 80%. The remaining approximately 20% comprises isomers of this tris-sulphochloride. To convert the product into the tris-sulphonic acid hydrazide mixture (analogously to Example 1), 49.4 g (0.1 mol) of the above tris-sulphochloride are reacted with a solution of 22.5 g (0.45 mol) of hydrazine hydrate in 200 g of water. After drying the product in vacuo at 35° C., 32.8 g of a mixture of 3,4'-ditolyl ether tris-sulphonic acid hydrazides are obtained. The product can be purified by dissolving in dilute sodium hydroxide solution and reprecipitating with dilute mineral acid. Melting point: 148° C., with decomposition.

EXAMPLE 3

59.4 g (0.3 mol) of 4,4'-ditolyl ether are introduced into 120 g of concentrated sulphuric acid, starting at room temperature. During the addition, the internal temperature rises to about 70° C. The mixture is heated to 110° to 115° C., this temperature is maintained for 45 minutes and the mixture is cooled to 50° C. and discharged onto 300 g of ice. The disulphonic acid is precipitated by adding 500 ml of saturated sodium chloride solution, the mixture is filtered, the residue is suspended in 300 ml of saturated sodium chloride solution, the suspension is neutralized with concentrated sodium hydroxide solution and filtered again and the residue is dried at 50° C. in vacuo. 129.3 g of a crude disodium salt of 4,4'-ditolyl ether-2,2'-disulphonic acid (ratio of carbon to sulphur:2.71; theory:2.62) are obtained.

To prepare the disulphochloride, 40 g of the crude disodium salt are introduced into 200 g of thionyl chloride at room temperature, 1 ml of dimethylformamide is added and the mixture is heated to 80° C. This temperature is maintained until the evolution of gas has ended, the excess thionyl chloride is then largely distilled off in vacuo and the mixture is discharged onto 200 g of ice. The precipitate is isolated, washed until neutral and dried. After recrystallization from xylene, 30.5 parts of 4,4'-ditolyl ether-2,2'-disulphochloride of melting point 211° to 213° C. are obtained.

To prepare the dihydrazide, 19.8 g of 4,4'-ditolyl ether-2,2'-disulphochloride are introduced into a mixture of 12.5 g of hydrazine hydrate and 25 g of ethanol at room temperature and the mixture is subsequently stirred at 45° to 50° C. for 2 hours. It is discharged onto 250 g of ice-water, acidified to a pH value of 5.5 with dilute sulphuric acid and filtered and the residue is washed with water until free from chloride. After drying at 35° C. in vacuo, 17.2 g of 4,4'-ditolyl ether-2,2'-disulphonic acid hydrazide of the formula

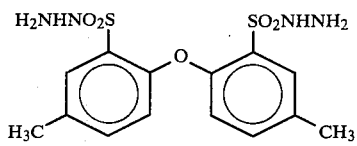

are obtained. This compound has a melting point of 172° C., with decomposition.

EXAMPLE 4

3,3'-Ditolyl ether-4,4'-disulphonic acid hydrazide of the formula

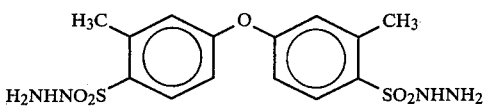

can be obtained from 3,3'-ditolyl ether in a manner analogous to that described in Example 3. Melting point: 151° C. (decomposition).

EXAMPLE 5

180 g of sulphuric acid monohydrate are warmed to 50°±2° C. in a 0.5 liter three-necked flask with a stirrer, dropping funnel and thermometer, and 36.8 g (0.2 mol) of 2-methyl-diphenyl ether are added dropwise at this temperature. The mixture is subsequently stirred for 1 hour and is discharged onto 400 g of ice-water, the reaction product is precipitated by adding 400 ml of saturated sodium chloride solution, the mixture is neutralized as described in Example 3 and the product is isolated and dried. 54.8 g of a crude disodium salt of 2-methyl-diphenyl ether-4,4'-disulphonic acid (ratio of carbon to sulphur:2.49; theory:2.43) are obtained.

49 g of the crude disodium salt of 2-methyl-diphenyl ether-4,4'-disulphonic acid are now further reacted with thionyl chloride and worked up, as described in Example 3. 41.5 g of a disulphochloride of the formula

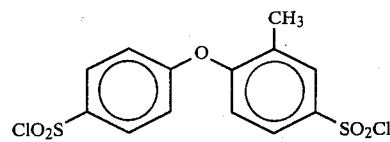

are obtained. Melting point: 120°–121° C. (from toluene).

The reaction of this disulphonic acid chloride with hydrazine hydrate is likewise carried out as described in Example 3. 31.8 g of 2-methyl-diphenyl ether-4,4'-disulphonic acid hydrazide are obtained from 38 g of disulphonic acid chloride. Melting point: 165° C. (decomposition). The compound can be recrystallized from aqueous ethanol.

USE EXAMPLES

EXAMPLE 6

The constituents of the mixture which are listed below were first mixed homogeneously in a mixing mill:

TABLE 1

|  | Mixture 1 | Mixture 2 |  |
|---|---|---|---|
| Natural rubber | 70.0 | 70.0 | parts by weight |
| Styrene resin | 30.0 | 30.0 | parts by weight |
| Zinc oxide | 3.0 | 3.0 | parts by weight |
| Kaolin | 10.0 | 10.0 | parts by weight |
| Magnesium carbonate | 10.0 | 10.0 | parts by weight |
| Paraffin wax | 0.5 | 0.5 | parts by weight |
| Stearic acid | 1.0 | 1.0 | parts by weight |
| Colourant (carbon black) | 0.2 | 0.2 | parts by weight |
| Sulphur | 2.5 | 2.5 | parts by weight |
| Dibenzothiazyl disulphide | 1.5 | 1.5 | parts by weight |
| 2,2'-Ditolyl ether-4,4'-disulphonic acid hydrazide | 7.5 | — | parts by weight |
| 3,3'-Ditolyl ether-4,4'-disulphonic acid hydrazide | — | 7.5 | parts by weight |

The finished mixtures were drawn to hides 10 mm thick and 430 g was punched out of each in a manner such that the material punched out could be inserted into a frame-type mould having the dimensions 200×200×8 mm (length of sides×height).

The mixtures-surrounded by the mould-were then pre-vulcanized at 140° C. and under a pressure of about 100 bars for 12 minutes in vulcanizing presses heated by steam. After this period of time, the presses were opened and the plates, which were now prevulcanized, expanded as a result of the gas pressure arising from the decomposition of the blowing agent. The cellular rubber plates were placed in hot air (under normal pressure) at 130° C. for a further 30 minutes for final complete vulcanisation. The plates thus obtained had the following values:

TABLE 2

|  | Density (g/cm$^3$) | Hardness (Shore A) |
|---|---|---|
| Mixture No. 1 | 0.19 | 20 |
| Mixture No. 2 | 0.21 | 22 |

After peeling off the vulcanization skin, the plates had a uniform, fine cellular structure and were virtually odourless.

EXAMPLE 7

The constituents of the mixture which are listed below were mixed homogeneously with one another in a mixing mill:

| | |
|---|---|
| Acrylonitrile/butadiene rubber | 70.0 parts by weight |
| Polyvinyl chloride | 30.0 parts by weight |
| Zinc oxide | 5.0 parts by weight |
| Carbon black | 35.0 parts by weight |
| Chalk | 25.0 parts by weight |
| Stearic acid | 1.0 parts by weight |
| Tricresyl phosphate | 25.0 parts by weight |
| Alkylsulphonic acid ester of phenol | 12.0 parts by weight |
| Sulphur | 1.5 parts by weight |
| Diphenylguanidine | 0.9 parts by weight |
| Tetramethylthiuram monosulphide | 0.4 parts by weight |
| Zinc N-dimethyldithiocarbamate | 0.2 parts by weight |
| 2,2'-Ditolyl ether-4,4'-disulphonic acid hydrazide | 20.0 parts by weight |

The finished mixture was drawn to a smooth hide 5 mm thick and test pieces 100×100 mm in size were punched out of this hide. These test pieces were placed in hot air (under normal pressure) at 140° C. for 20 minutes for the purpose of vulcanization and simultaneous expansion. After this period, the test pieces were completely vulcanized and exhibited a considerable increase in volume compared with the non-vulcanized test pieces. The density was determined as 0.13 g/cm$^3$.

EXAMPLE 8

A PVC plastisol (a paste of PVC and plasticiser) of the following composition: 50.0 g of PVC paste, K value 70 (pH of the aqueous extract=7.0), 50.0 g of di-2-ethyl-hexyl phthalate, 0.3 g of diphenylthiourea and 10.0 g of 2,2'-dimethyl-diphenyl ether-4,4'-disulphonic acid hydrazide is introduced into a gas-tight steel mould 100×100×10 mm in size and is compression-moulded under a high-pressure press under 25 bars at 170° C. for 10 minutes. It is then cooled under pressure for 7 minutes. The resulting moulded article is then subsequently heated in hot air at 105° C. for 30 minutes and expanded.

A finely porous foamed block with a density of 93 kg/m$^3$ is obtained. No scorching of the core is to be observed.

EXAMPLE 9

A PVC plastisol consisting of: 50.0 g of a polyvinyl chloride which can be made into a paste and has a K value of 70, according to DIN 53 726 (determination of the viscosity number and of the K value of polyvinyl chloride in solution); pH of the aqueous extract=7.0, 38.0 g of di-2-ethyl-hexyl phthalate, 12.0 g of butyl-benzyl phthalate, 0.5 g of a commercially available cadmium/zinc stabilizer and 2.0 g of 2,2'-dimethyl-diphenyl ether-4,4'-disulphonic acid hydrazide is foamed in a hot air tunnel heated with hot air at 190° C., under a load of 850 g/m$^2$ and with a residence time of 1 minute. A finely porous foam with a specific gravity of 420 kg/m$^3$ is obtained.

EXAMPLE 10

In comparison, the plastisol from Example 9 with 2.0 parts by weight of diphenyl ether-4,4'-disulphonic acid hydrazide as the blowing agent gives a foam with a specific gravity of 500 kg/m$^3$.

What is claimed is:

1. A di- or tri-sulphonic acid hydrazide of an alkylated diphenyl ether, said hydrazide being of the formula

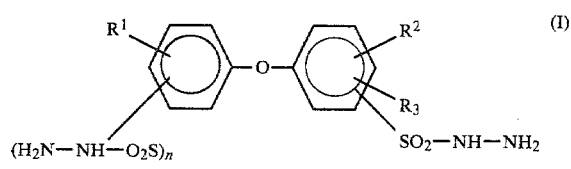

wherein
R$_1$ and R$_2$ are identical or different and represent halogen or a lower alkyl radical and R$_1$ or R$_2$ can denote hydrogen,
R$_3$ denotes a lower alkyl radical and
n represents the number 1 or 2.

2. A di-sulphonic acid hydrazide according to claim 1 of the formula

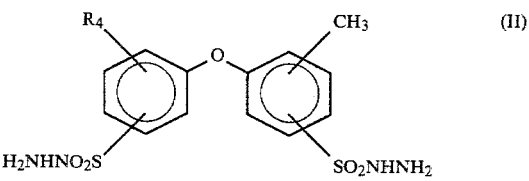

wherein R$_4$ represent hydrogen, chlorine or methyl.

3. A di-sulphonic acid hydrazide according to claim 1 which is 2,2'-ditolyl ether-4,4'-disulphonic acid hydrazide.

4. A di-sulphonic acid hydrazide according to claim 1, which is 3,3'-ditolyl ether-4,4'-di-sulphonic acid hydrazide.

5. A di-sulphonic acid hydrazide according to claim 1, which is 4,4'-ditolyl ether-2,2'-di-sulphonic acid hydrazide.

6. A di- or tri-sulphonic acid hydrazide of claim 1, which is a di- or tri-sulphonic acid hydrazide of 3,4'-ditolyl ether.

7. A hydrazide according to claim 1, which is 2-methyl-diphenyl ether-4,4'-disulphonic acid hydrazide.

8. A process for the preparation of an alkyl-diphenyl ether sulphonic acid hydrazide which comprises contacting an alkyl-diphenyl ether with sulphuric acid at a temperature in the range from 20° to 150° C. thereafter contacting the so sulphonated product with an acid chloride whereby to form an alkyl-diphenyl ether disulphonic acid chloride and thereafter contacting said disulphonic acid chloride with hydrazine in a solvent mixture at a temperature in the range from 0° to 100° C.

* * * * *